United States Patent
Kang et al.

(10) Patent No.: US 10,485,479 B2
(45) Date of Patent: Nov. 26, 2019

(54) GRIP-TYPE BLOOD PRESSURE MEASURING APPARATUS AND METHOD OF OPERATING THE SAME

(71) Applicant: SAMSUNG ELECTRONICS CO., LTD., Suwon-si (KR)

(72) Inventors: Jae Min Kang, Seoul (KR); Yong Joo Kwon, Yongin-si (KR); Sun Kwon Kim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 550 days.

(21) Appl. No.: 15/204,593

(22) Filed: Jul. 7, 2016

(65) Prior Publication Data

US 2017/0014036 A1   Jan. 19, 2017

(30) Foreign Application Priority Data

Jul. 16, 2015 (KR) .................. 10-2015-0101202

(51) Int. Cl.
*A61B 5/00* (2006.01)
*A61B 5/021* (2006.01)
*A61B 5/024* (2006.01)

(52) U.S. Cl.
CPC ........ *A61B 5/6825* (2013.01); *A61B 5/02125* (2013.01); *A61B 5/02416* (2013.01); *A61B 5/02444* (2013.01); *A61B 2562/043* (2013.01)

(58) Field of Classification Search
CPC . A61B 5/021; A61B 5/02108; A61B 5/02116; A61B 5/02125; A61B 5/02141; A61B 5/02416; A61B 5/02427; A61B 5/02433; A61B 5/02438; A61B 5/02444; A61B 5/0285; A61B 5/0295; A61B 5/6825; A61B 5/6826; A61B 5/6887; A61B 5/6893; A61B 5/6897; A61B 5/6898; A61B 2560/0418; A61B 2560/0425; A61B 2562/0238; A61B 2562/04; A61B 2562/043

See application file for complete search history.

(56) References Cited

U.S. PATENT DOCUMENTS 8,313,439 B2   11/2012  McCombie et al.
8,784,325 B2    7/2014  Kim et al.
(Continued)

FOREIGN PATENT DOCUMENTS

JP   2010-220690 A   10/2010
JP   2014-188237 A   10/2014
(Continued)

*Primary Examiner* — Eugene T Wu
(74) *Attorney, Agent, or Firm* — Sughrue Mion, PLLC

(57) ABSTRACT

A grip-type blood pressure measuring apparatus and a method of operating the apparatus are provided. The grip-type blood pressure measuring apparatus may include a pulse wave measuring sensor array comprising a plurality of pulse wave measuring sensors that are spaced apart from each other at a predetermined interval; and a blood pressure measurer configured to select a first pulse wave and a second pulse wave from among a plurality of pulse waves measured by the plurality of pulse wave measuring sensors, analyze the selected first pulse wave and second pulse wave, and determine a blood pressure based on an analysis result of the first pulse wave and the second pulse wave.

17 Claims, 8 Drawing Sheets

(56) References Cited

U.S. PATENT DOCUMENTS

| | | |
|---|---|---|
| 2012/0071768 A1 | 3/2012 | Yamakoshi et al. |
| 2013/0012823 A1 | 1/2013 | Ripoll et al. |
| 2014/0051941 A1* | 2/2014 | Messerschmidt .... A61B 5/6898 600/301 |
| 2014/0114201 A1 | 4/2014 | Watanabe et al. |
| 2015/0320328 A1* | 11/2015 | Albert ................. A61B 5/0402 600/480 |
| 2016/0058312 A1* | 3/2016 | Han ....................... G01N 21/55 600/473 |

FOREIGN PATENT DOCUMENTS

| | | |
|---|---|---|
| JP | 2015-54223 A | 3/2015 |
| KR | 10-2009-027390 A | 3/2009 |

\* cited by examiner

GRIP-TYPE BLOOD PRESSURE MEASURING APPARATUS AND METHOD OF OPERATING THE SAME

CROSS-REFERENCE TO RELATED APPLICATION

This application claims priority from Korean Patent Application No. 10-2015-0101202, filed on Jul. 16, 2015 in the Korean Intellectual Property Office, the disclosure of which is incorporated herein by reference in its entirety.

BACKGROUND

1. Field

Apparatuses and methods consistent with exemplary embodiments relate to a blood pressure measuring technology, and more particularly to a grip-type blood pressure measuring apparatus and a method of operating the same.

2. Description of the Related Art

With a growing interest in personal health, various types of biometric data detection devices are being developed.

A cuff-less blood pressure sensor may measure blood pressure using an indirect measurement method. For example, the sensor may measure the blood pressure by determining a Pulse Transit Time (PTT) from an optical signal and an electrocardiogram (ECG) signal, or by using a Pulse Wave Analysis (PWA) method that analyzes pulse waves based on the optical signal.

However, the PTT method is cumbersome in that an ECG signal is further needed in addition to a pulse wave signal, and touches of both hands are required. Further, the PWA method, which analyzes only a waveform of pulse waves, may not enable accurate blood pressure measurement.

SUMMARY

Exemplary embodiments address at least the above problems and/or disadvantages and other disadvantages not described above. Also, the exemplary embodiments are not required to overcome the disadvantages described above, and may not overcome any of the problems described above.

According to an aspect of an exemplary embodiment, there is provided a grip-type blood pressure measuring apparatus, including: a pulse wave measuring sensor array including a plurality of pulse wave measuring sensors that are spaced apart from each other at a predetermined interval; and a blood pressure measurer configured to select a first pulse wave and a second pulse wave from among a plurality of pulse waves measured by the plurality of pulse wave measuring sensors, and analyze the selected first pulse wave and second pulse wave, and determine a blood pressure based on an analysis result of the first pulse wave and the second pulse wave.

The grip-type blood pressure measuring apparatus may have a cylinder shape, and the pulse wave measuring sensor array may be a ring type array arranged to surround a side surface of the grip-type blood pressure measuring apparatus.

The plurality of pulse wave measuring sensors may emit light to a subject, detect the light reflected from the subject, and obtain the plurality of pulse waves from the detected light.

The blood pressure measurer may include: a pulse wave selector configured to select the first pulse wave and the second pulse wave from among the plurality of pulse waves measured by the plurality of pulse wave measuring sensors; a feature point extractor configured to extract a first feature point from the first pulse wave and extract a second feature point corresponding to the first feature point from the second pulse wave; and a blood pressure calculator configured to calculate the blood pressure based on the first feature point and the second feature point.

The pulse wave selector may be further configured to detect a start point and an end point of pulse wave detection of the subject according to a movement of the plurality of pulse waves, and may select a pulse wave measured at the start point of the pulse wave detection as the first pulse wave and a pulse wave measured at the end point of the pulse wave detection as the second pulse wave.

The blood pressure calculator may be further configured to calculate a pulse wave velocity based on the first feature point and the second feature point, and may calculate blood pressure based on the calculated pulse wave velocity and a blood pressure estimation equation.

The blood pressure calculator may be further configured to calculate a time difference between the first feature point and the second feature point, calculate a distance between a point where the first pulse wave is measured and a point where the second pulse wave is measured, and obtain the pulse wave velocity by dividing the distance by the time difference.

The grip-type blood pressure measuring apparatus may further include a user interface configured to output information on the blood pressure.

The grip-type blood pressure measuring apparatus may further include a communicator configured to transmit the information on the blood pressure to an external device.

The grip-type blood pressure measuring apparatus may further include a driver configured to generate a driving signal to drive the grip-type blood pressure measuring apparatus by sensing whether a user grips the grip-type blood pressure measuring apparatus.

According to an aspect of another exemplary embodiment, there is provided a method of operating a grip-type blood pressure measuring apparatus, the method including: measuring pulse waves by using a pulse wave measuring sensor array comprising a plurality of pulse wave measuring sensors that are spaced apart from each other at a predetermined interval; selecting a first pulse wave and a second pulse wave from among a plurality of pulse waves measured by the plurality of pulse wave measuring sensors; analyzing the selected first pulse wave and second pulse wave; and determining a blood pressure based on an analysis result of the first pulse wave and the second pulse wave.

The grip-type blood pressure measuring apparatus may have a cylinder shape, and the pulse wave measuring sensor array may be a ring type array arranged to surround a side surface of the grip-type blood pressure measuring apparatus.

The selecting the first pulse wave and the second pulse wave may include: detecting a start point and an end point of the pulse wave detection of a subject according to a movement of the plurality of pulse waves; selecting a pulse wave measured at the start point of the pulse wave detection as the first pulse wave; and selecting a pulse wave measured at the end point of pulse wave detection as the second pulse wave.

The determining the blood pressure may include: extracting a first feature point from the first pulse wave; extracting a second feature point corresponding to the first feature point from the second pulse wave; and determining the blood pressure based on the first feature point and the second feature point.

The determining the blood pressure may include: calculating a pulse wave velocity based on the first feature point and the second feature point; and calculating the blood pressure based on the calculated pulse wave velocity and a blood pressure estimation equation.

The calculating the pulse wave velocity may include: calculating a time difference between the first feature point and the second feature point; and dividing, by the calculated time difference, a distance between a point where the first pulse wave is measured and a point where the second pulse wave is measured.

The method of operating a grip-type blood pressure measuring apparatus may further include generating a driving signal to drive the grip-type blood pressure measuring apparatus by sensing whether a user grips the grip-type blood pressure measuring apparatus.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
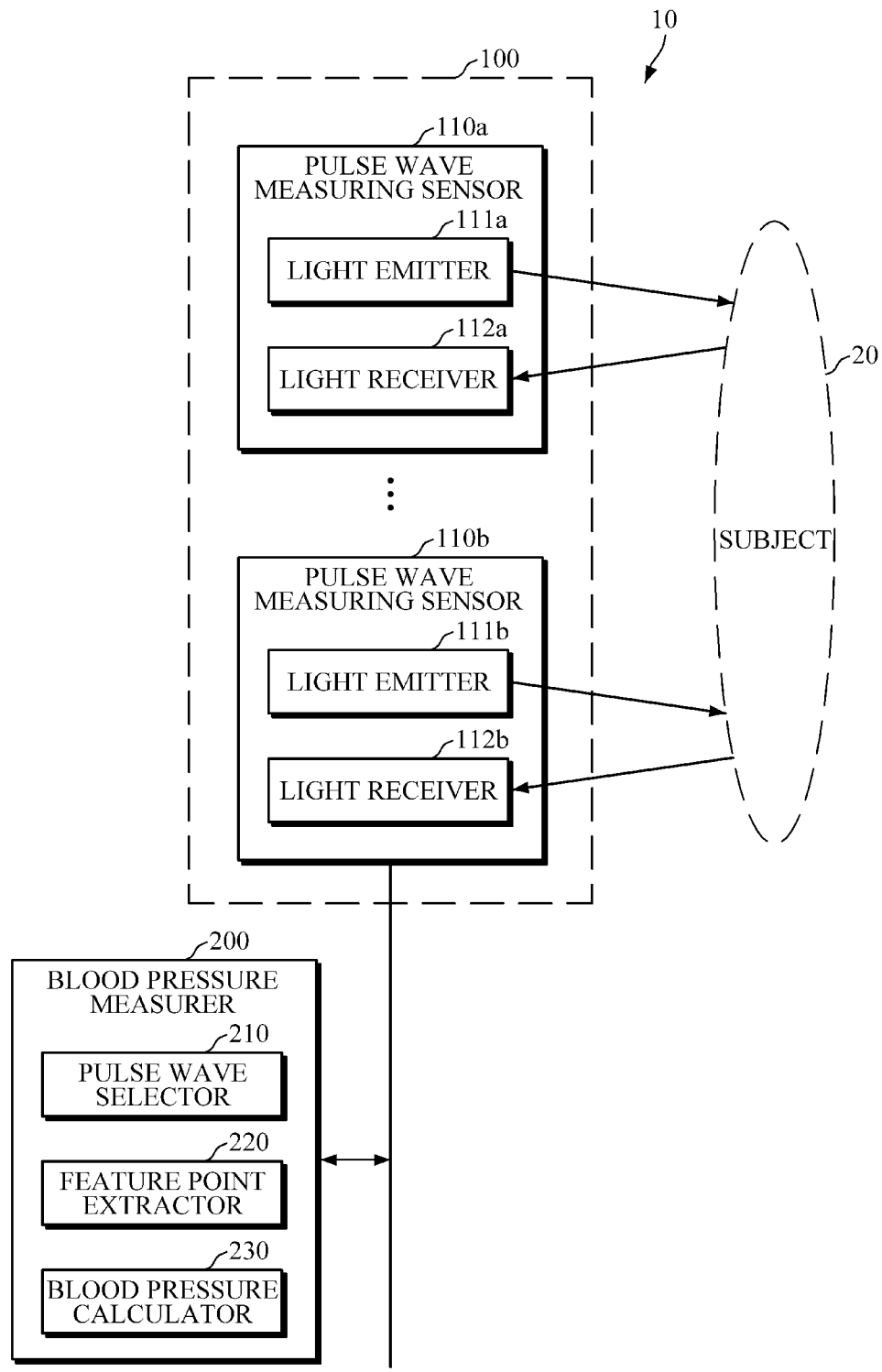
FIG. 1 is a block diagram illustrating an example of a grip-type blood pressure measuring apparatus.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

FIG. 1 is a block diagram illustrating an example of a grip-type blood pressure measuring apparatus.

The grip-type blood pressure measuring apparatus 10 measures blood pressure of a subject. For example, the apparatus 10 may measure a blood pressure using an indirect measurement method. That is, the grip-type blood pressure measuring apparatus 10 is a cuff-less type blood pressure measuring apparatus, which measures blood pressure by emitting light to a subject, i.e., a user's body part gripping the grip-type blood pressure measuring apparatus 10, measuring pulse waves by sensing reflected or scattered light, and analyzing the measured pulse waves.

The grip-type blood pressure measuring apparatus 10 may be various grip-type devices that may be gripped by a user. For example, the grip-type blood pressure measuring apparatus 10 may be a steering wheel of a vehicle, a handle grip of various tools (e.g., door, bat, golf club, tennis racket, etc.), and the like. However, the grip-type blood pressure measuring apparatus 100 is merely exemplary and is not limited thereto.

Referring to FIG. 1, the grip-type blood pressure measuring apparatus 10 includes a pulse wave measuring sensor array 100 and a blood pressure measurer 200.

The pulse wave measuring sensor array 100 may include a plurality of pulse wave measuring sensors 110a and 110b. The pulse wave measuring sensors 110a and 110b may be spaced apart from each other at a predetermined interval. The pulse wave measuring sensor array 100 may be a one-dimensional array, but is not limited thereto, and may be a two-dimensional array according to performance and purpose of use of a system.

The pulse wave measuring sensor 110a may include a light emitter 111a and a light receiver 112a, and the pulse wave measuring sensor 110b may include a light emitter 110b and a light receiver 112b.

The light emitters 111a and 111b may emit light to a subject 20, and the light receivers 112a and 112b may detect light scattered or reflected from the subject 20. The pulse wave measuring sensors 110a and 110b may acquire pulse waves from a detected optical signal. That is, the pulse wave measuring sensor array 100 may measure pulse waves at various points by using the pulse wave measuring sensors 110a and 110b. For example, the pulse wave measuring sensors 110a and 110b may be arranged regularly or irregularly, or periodically or non-periodically to form the pulse wave measuring sensor array 100.

In one exemplary embodiment, a light emitting diode (LED) or a laser diode may be used as the light emitters 111a and 111b, and a photo diode, a photo transistor (PTr), or a charge-couple device (CCD) may be used as the light receivers 112a and 112b.

The pulse wave measuring sensor array 100 may be a ring type array arranged to surround the external surface of the grip-type blood pressure measuring apparatus 10. In another example, the pulse wave measuring sensor array 100 may be configured in various manners according to the shape of the grip-type blood pressure measuring apparatus 10.

The configuration and arrangement of the pulse wave sensor array 100 will be described later with reference to FIGS. 2A and 2B.

The subject 20 is a blood pressure measuring target, and may be a body portion that may contact or may be adjacent to the pulse wave measuring sensor array 100 of the grip-type blood pressure measuring apparatus 10, or a body portion on which pulse waves may be easily measured by using photoplethysmography (PPG). For example, the subject 20 may be a hand of a human body gripping the grip-type blood pressure measuring apparatus 10. The grip-type blood pressure measuring apparatus 10 may have a cylinder shape.

The blood pressure measurer 200 may measure blood pressure by analyzing two pulse waves (hereinafter referred to as a first pulse wave and a second pulse wave) among a plurality of pulse waves measured by the pulse wave measuring sensors 110a and 110b. To this end, the blood pressure measurer 200 includes a pulse wave selector 210, a feature point extractor 220, and a blood pressure calculator 230. The blood pressure measurer 200 may be implemented by one or more processors.

The pulse wave selector 210 may select the first pulse wave and the second pulse wave from among a plurality of pulse waves measured by the pulse wave measuring sensors 110a and 110b.

In one exemplary embodiment, based on the plurality of pulse waves measured by the pulse wave measuring sensors 110a and 110b, the pulse wave selector 210 may detect a start point and an end point of pulse wave detection of a subject according to movement of pulse waves, and may select a pulse wave measured at the start point of pulse wave detection as the first pulse wave, and a pulse wave measured at the end point of pulse wave detection as the second pulse wave.

For example, it is assumed that eight pulse wave measuring sensors (first pulse wave measuring sensor to eighth pulse wave measuring sensor) are arranged to surround the external surface of the grip-type blood pressure measuring apparatus 10 to form a pulse wave measuring sensor array. A user may grip the grip-type blood pressure measuring apparatus 10 such that the user's hand touches the fourth pulse wave measuring sensor to the eighth pulse wave measuring sensor. For example, the palm side of the wrist may touch the fourth pulse wave measuring sensor, and a fingertip of the user may touch the eighth pulse wave measuring sensor. According to the movement of pulse waves from the palm side of the wrist to the fingertips, pulse waves are detected sequentially from the fourth pulse wave measuring sensor to the eighth pulse wave measuring sensor. In this case, a point where the fourth pulse wave measuring sensor first detects a pulse wave is a start point of pulse wave detection, and a point where the eighth pulse wave measuring sensor lastly detects a pulse wave is an end point of pulse wave detection. The pulse wave selector 210 may select a pulse wave measured by the fourth pulse wave measuring sensor as the first pulse wave, and may select a pulse wave measured by the eighth pulse wave measuring sensor as the second pulse wave.

The feature point extractor 220 may extract a feature point from the first pulse wave (hereinafter referred to as a first feature point), and may extract a feature point corresponding to the first feature point from the second pulse wave (hereinafter referred to as a second feature point), in which the feature points may include a start point, a maximum point, a minimum point, and the like.

The blood pressure calculator 230 may calculate blood pressure based on the first feature point and the second feature point. For example, the blood pressure calculator 230 may calculate a pulse wave velocity based on the first feature point and the second feature point, and may calculate blood pressure based on the calculated pulse wave velocity and a blood pressure estimation equation. The blood pressure estimation equation defines a relationship between blood pressure and the pulse wave velocity, and may be stored in a database or in an external memory.

Figure 2A:
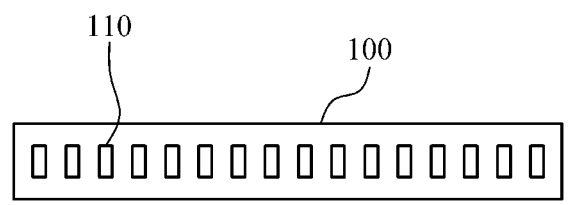
FIG. 2A is a diagram illustrating an example of a pulse wave measuring sensor array 100.
Figure 2B:
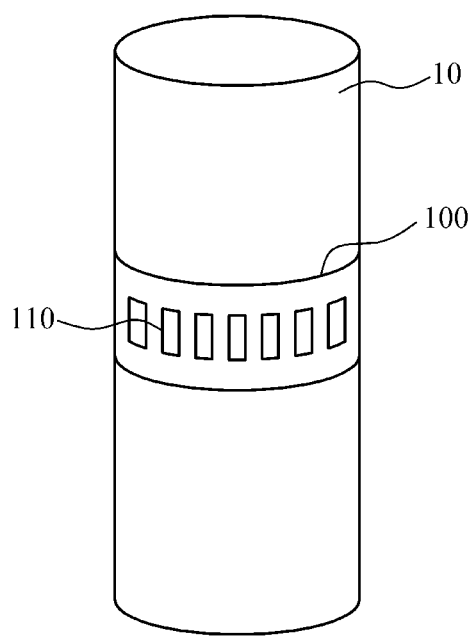
FIG. 2B is a diagram illustrating an example of an arrangement of the pulse wave measuring sensor array 100 illustrated in FIG. 2A.

FIG. 2A is a diagram illustrating an example of a pulse wave measuring sensor array 100, and FIG. 2B is a diagram illustrating an example of an arrangement of the pulse wave measuring sensor array 100 illustrated in FIG. 2A.

As illustrated in FIGS. 2A and 2B, the pulse wave measuring sensor array 100 may include a plurality of pulse wave measuring sensors 110 arranged in a one-dimensional array. Further, the pulse wave measuring sensor array 100 may be arranged to surround the external surface of the grip-type blood pressure measuring apparatus 10, i.e., a portion gripped by a user.

Figure 3A:
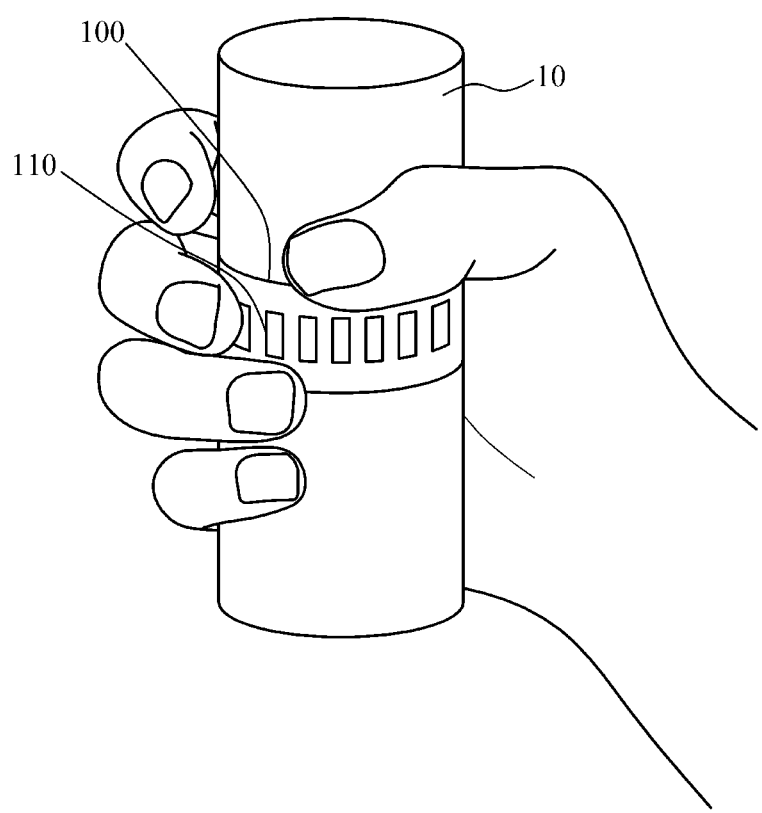
FIG. 3A and FIG. 3B are diagrams illustrating examples in which a grip-type blood pressure measuring apparatus 10 is applied.
Figure 3B:
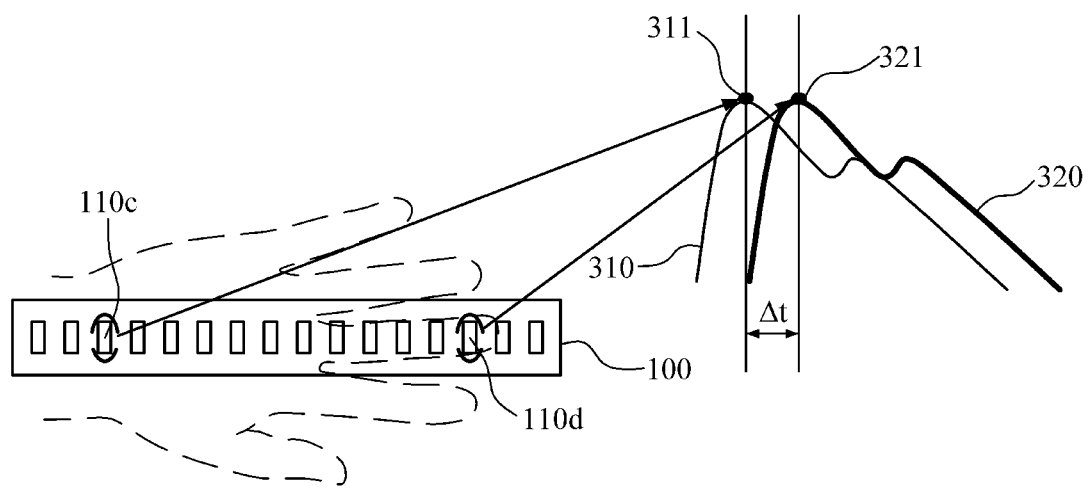

FIG. 3A and FIG. 3B are diagrams illustrating examples in which a grip-type blood pressure measuring apparatus 10 is applied.

Referring to FIGS. 3A and 3B, once a user grips the grip-type blood pressure measuring apparatus 10, a portion from the palm side of the wrist to the fingertips touches one or more sensors among a plurality of pulse wave measuring sensors of the pulse wave measuring sensor array 100. The plurality of pulse wave measuring sensors of the pulse wave measuring sensor array 100 emits light to a body portion which touches the sensor, i.e., a subject, and detects light scattered or reflected from the subject to acquire pulse waves from a detected optical signal.

The pulse wave selector 210 detects a start point and an end point of pulse wave detection, and selects the first pulse wave measured at the start point of pulse wave detection and the second pulse wave measured at the end point of pulse wave detection.

A waveform 310 represents the first pulse wave measured at the start point of pulse wave detection, i.e., a pulse wave measured by the pulse wave measuring sensor 110c that contacts the palm side of the wrist, and a waveform 320 is the second pulse wave measured at the end point of pulse wave detection, i.e., a pulse wave measured by the pulse wave measuring sensor 110d that contacts a fingertip.

The feature point extractor 220 may extract the first feature point 311 from the first pulse wave, and may extract the second feature point 321 corresponding to the first feature point 311 from the second pulse wave.

The blood pressure calculator 230 may calculate a pulse wave velocity by calculating a time difference $\Delta t$ between the first feature point 311 and the second feature point 321, and by dividing a distance between the pulse wave measuring sensor 110c and the pulse wave measuring sensor 110d by the calculated time difference $\Delta t$.

Since the pulse wave velocity is increased when blood vessel elasticity is reduced, the pulse wave velocity may be a good indicator to show the blood vessel elasticity and a change in blood pressure, and may be used to establish a correlation between the pulse wave velocity and blood pressure.

The blood pressure calculator 230 may calculate blood pressure based on a blood pressure estimation equation that defines a relationship between the pulse wave velocity and blood pressure, in which the blood pressure estimation equation may be stored in a database or in an external memory.

Figure 4:
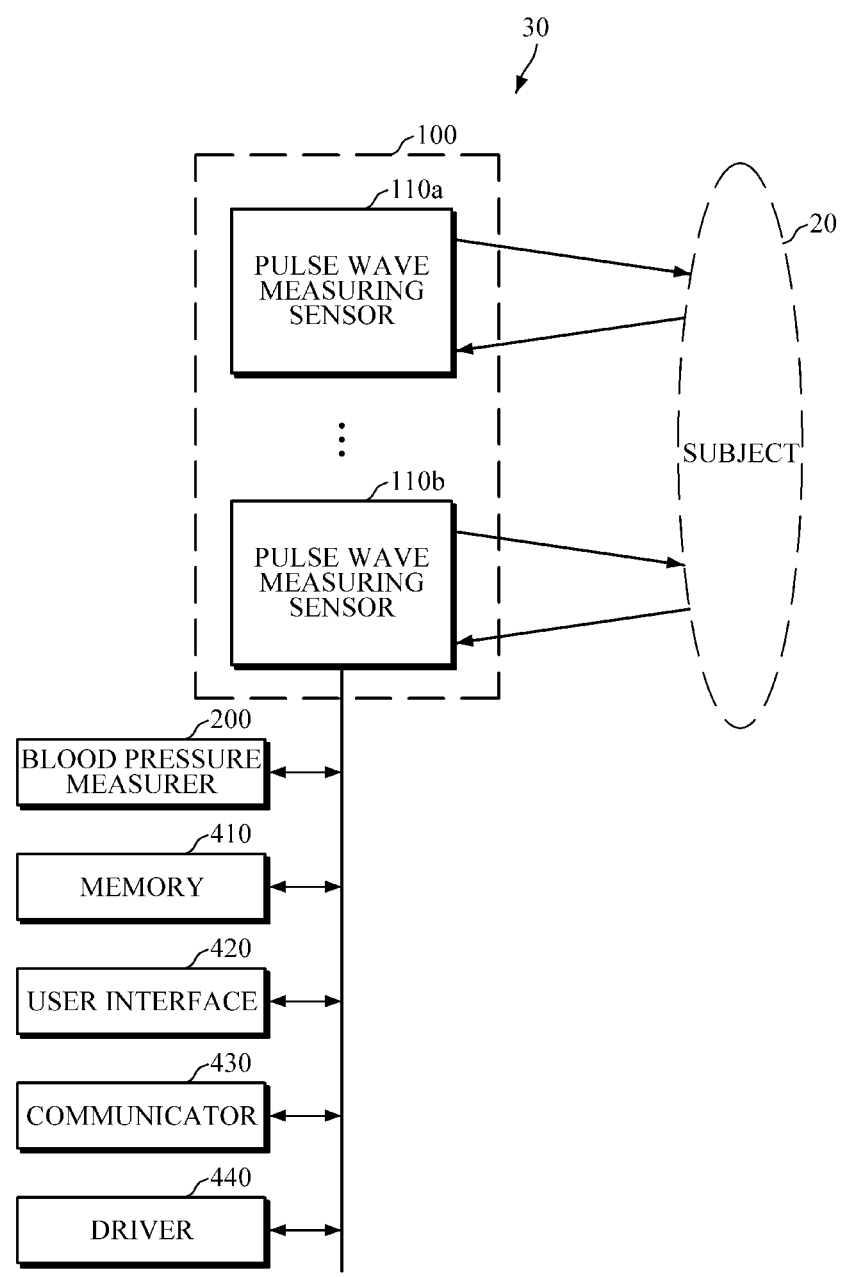
FIG. 4 is a block diagram illustrating another example of a grip-type blood pressure measuring apparatus.

FIG. 4 is a block diagram illustrating another example of a grip-type blood pressure measuring apparatus.

Referring to FIG. 4, as compared to the grip-type blood pressure measuring apparatus 10 illustrated in FIG. 1, a grip-type blood pressure measuring apparatus 30 illustrated in FIG. 4 may further include a memory 410, a user interface 420, a communicator 430, and a driver 440 selectively.

The memory 410 may store programs to process and control the blood pressure measurer 200 and may store input/output data. For example, the memory 410 may store programs for pulse wave analysis and blood pressure calculation performed by the blood pressure measurer 200, and/or information on a blood pressure estimation equation. Further, the memory 410 may store pulse wave measurement results of the pulse wave measuring sensors 110a and 110b to be used for the processing at the blood pressure measurer 200.

The memory 410 may include at least one storage medium among flash memory type, hard disk type, multimedia card micro type, card type memory (e.g., secure digital (SD) or XD memory, etc.), random access memory (RAM), static random access memory (SRAM), read-only memory (ROM), electrically erasable programmable read only memory (EEPROM), programmable read only memory (PROM), magnetic memory, magnetic disks, optical discs, and the like.

The user interface 420 is an interface between the grip-type blood pressure measuring apparatus 30 and a user, and/or an interface between the grip-type blood pressure measuring apparatus 30 and other external device, and may include an input and an output. The user may be a blood pressure measuring target, i.e., the subject 20, but may be a concept wider than the subject 20, including a medical expert, who may use the grip-type blood pressure measuring apparatus 30.

Information that may be necessary for operating the grip-type blood pressure measuring apparatus 30 is input through the user interface 420, and measurement results of blood pressure may be output through the user interface 420. The user interface 420 may include, for example, a button, a connector, a keypad, a display, and the like, and may further include a sound output component or a vibration motor.

The communicator 430 may communicate with external devices. For example, the communicator 430 may transmit measurement results of blood pressure to an external device, or may receive various types of information useful for measuring blood pressure from an external device.

The external device may be medical equipment using information on the measured blood pressure, a printer to print out results, or a display to display information on the measured blood pressure. In addition, the external device may be a smartphone, a mobile phone, a personal digital assistant (PDA) device, a laptop computer, a personal computer (PC), and other mobile or non-mobile computing devices.

The communicator 430 may communicate with external devices based on Bluetooth communication, Bluetooth Low Energy communication, Near Field Communication (NFC), WLAN communication, Zigbee communication, Infrared Data Association (IrDA) communication, Wi-Fi Direct (WFD) communication, Ultra Wideband (UWB) communication, Ant+ communication, Wi-Fi communication, Radio Frequency IDentification (RFID) communication, and the like. However, the communicator 430 is merely exemplary, and is not limited thereto.

The driver 440 may generate a driving signal to drive the grip-type blood pressure measuring apparatus 30 by sensing whether a user grips the grip-type blood pressure measuring apparatus 30 or not. However, the driver 440 is not limited thereto. That is, the driver 440 may generate a driving signal even in response to a driving instruction received from a user through the user interface 420, and the like.

Figure 5:
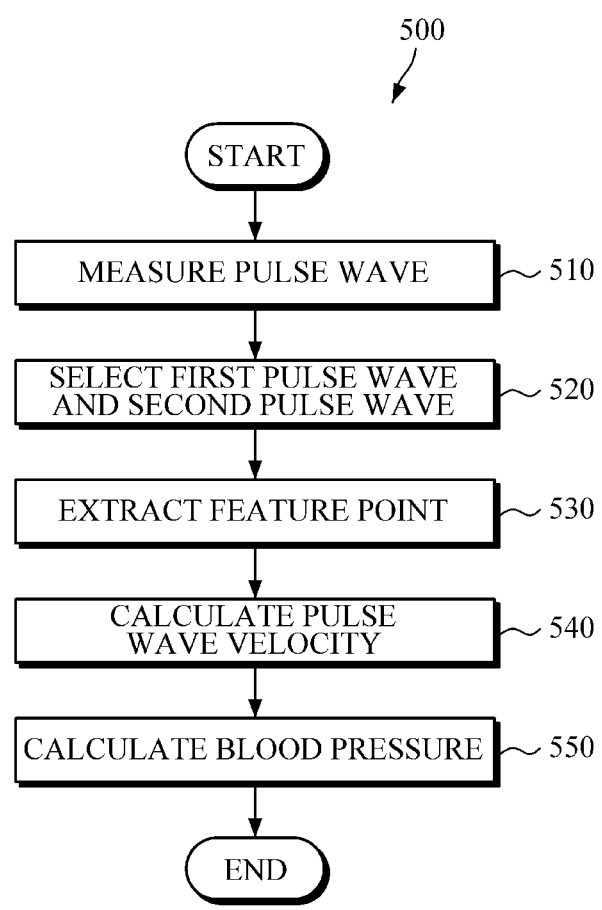
FIG. 5 is a flowchart illustrating an example of a method of operating the grip-type blood pressure measuring apparatus 10.

FIG. 5 is a flowchart illustrating an example of a method of operating the grip-type blood pressure measuring apparatus 10.

Referring to FIGS. 1 and 5, the grip-type blood pressure measuring apparatus 10 measures pulse waves in operation 510 by using the pulse wave measuring sensor array 100 arranged to surround the external surface of the grip-type blood pressure measuring apparatus 10. In this case, the pulse wave measuring sensor array 100 may include a plurality of pulse wave measuring sensors 110a and 110b that are spaced apart at a predetermined interval.

The grip-type blood pressure measuring apparatus 10 may select the first pulse wave and the second pulse wave among a plurality of pulse waves measured by the pulse wave measuring sensors 110a and 110b in operation 520.

In one exemplary embodiment, the grip-type blood pressure measuring apparatus 10 may detect a start point and an end point of pulse wave detection of a subject according to the movement of pulse waves based on the plurality of measured pulse waves, and may select a pulse wave measured at the start point of pulse wave detection as the first pulse wave and a pulse wave measured at the end point of pulse wave detection as the second pulse wave.

The grip-type blood pressure measuring apparatus 10 may extract a first feature point from the first pulse wave, and may extract a second feature point corresponding to the first feature point from the second pulse wave in operation 530. In this case, the feature points may include a start point, a maximum point, a minimum point, and the like.

The grip-type blood pressure measuring apparatus 10 may calculate a pulse wave velocity based on the first feature point and the second feature point in operation 540. In one exemplary embodiment, the grip-type blood pressure measuring apparatus 10 may calculate a pulse wave velocity by calculating a time difference $\Delta t$ between the first feature point and the second feature point, and by dividing a distance between the start point of pulse wave detection where the first pulse wave is measured and the end point of pulse wave detection where the second pulse wave is measured by the calculated time difference $\Delta t$.

The grip-type blood pressure measuring apparatus 10 may calculate blood pressure based on a blood pressure estimation equation that defines a relationship between blood pressure and the pulse wave velocity in operation 550. The blood pressure estimation equation may be stored in a database or in an external memory.

Figure 6:
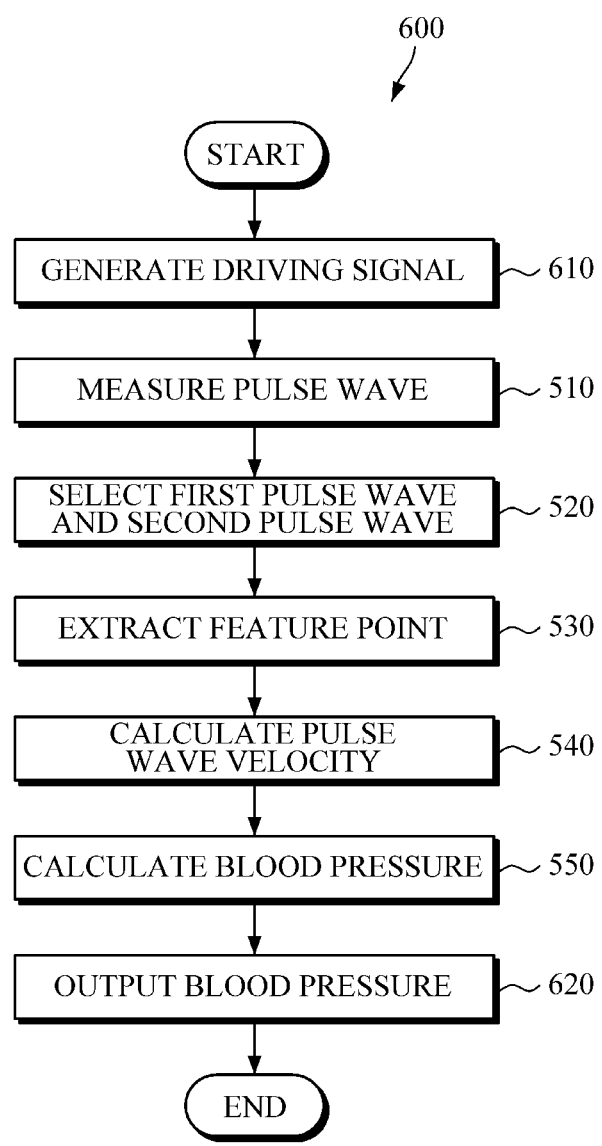
FIG. 6 is a flowchart illustrating another example of a method of operating the grip-type blood pressure measuring apparatus 10.

FIG. 6 is a flowchart illustrating another example of a method of operating the grip-type blood pressure measuring apparatus 30.

Upon comparison of FIG. 6 with FIG. 5, the method 600 of operating the grip-type blood pressure measuring apparatus 30 illustrated in FIG. 6 may further include generating a driving signal in operation 610 and displaying in operation 620.

Referring to FIGS. 4 and 6, in the method 600, the grip-type blood pressure measuring apparatus 30 senses whether a user grips the grip-type blood pressure measuring apparatus 30, and generates a driving signal to drive the grip-type blood pressure measuring apparatus 30 in operation 610.

In displaying in operation 620, the grip-type blood pressure measuring apparatus 30 outputs, through the user interface 420, the blood pressure calculated in operation 550.

The present disclosure can be realized as a computer-readable code written on a computer-readable recording medium. Codes and code segments needed for realizing the present disclosure can be easily deduced by computer programmers of ordinary skill in the art. The computer-readable recording medium may be any type of recording device in which data is stored in a computer-readable manner. Examples of the computer-readable recording medium include a ROM, a RAM, a CD-ROM, a magnetic tape, a floppy disc, an optical disk, and the like. Further, the computer-readable recording medium can be distributed over a plurality of computer systems connected to a network so that a computer-readable recording medium is written thereto and executed therefrom in a decentralized manner.

Also, the operations or steps of the methods or algorithms according to the above exemplary embodiments may be written as a computer program transmitted over a computer-readable transmission medium, such as a carrier wave, and received and implemented in general-use or special-purpose digital computers that execute the programs. Moreover, it is understood that in exemplary embodiments, one or more units (e.g., those represented by a block as illustrated in FIGS. 1 and 4) of the above-described apparatuses and devices can include or implemented by circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A method of operating a grip-type blood pressure measuring apparatus, the method comprising:
   measuring pulse waves by using a pulse wave measuring sensor array comprising a plurality of pulse wave measuring sensors that are spaced apart from each other at a predetermined interval and are arranged on an external surface of a ring-type strip that is curved in a three-dimensional space to have a three-dimensional shape;
   obtain a plurality of pulse waves from the plurality of pulse wave measuring sensors when the plurality of pulse wave measuring sensors on the ring-type strip are in contact with a user;
   selecting a first pulse wave and a second pulse wave from among the plurality of pulse waves;
   analyzing the selected first pulse wave and second pulse wave; and
   determining a blood pressure based on an analysis result of the first pulse wave and the second pulse wave.

2. The method of claim 1, wherein the determining the blood pressure comprises:
   extracting a first feature point from the first pulse wave;
   extracting a second feature point corresponding to the first feature point from the second pulse wave; and
   determining the blood pressure based on the first feature point and the second feature point.

3. The method of claim 2, wherein the determining the blood pressure comprises:
   calculating a pulse wave velocity based on the first feature point and the second feature point; and
   calculating the blood pressure based on the calculated pulse wave velocity and a blood pressure estimation equation.

4. The method of claim 3, wherein the calculating the pulse wave velocity comprises:
   calculating a time difference between the first feature point and the second feature point; and
   dividing, by the calculated time difference, a distance between a point where the first pulse wave is measured and a point where the second pulse wave is measured.

5. The method of claim 1, wherein the selecting the first pulse wave and the second pulse wave comprises:
   detecting a start point and an end point of pulse wave detection of a subject according to a movement of the plurality of pulse waves;
   selecting a pulse wave measured at the start point of the pulse wave detection as the first pulse wave; and
   selecting a pulse wave measured at the end point of the pulse wave detection as the second pulse wave.

6. The method of claim 1, further comprising generating a driving signal to drive the grip-type blood pressure measuring apparatus by sensing whether the user grips the grip-type blood pressure measuring apparatus.

7. A method of operating a grip-type blood pressure measuring apparatus, the method comprising:
   measuring pulse waves by using a pulse wave measuring sensor array comprising a plurality of pulse wave measuring sensors that are spaced apart from each other at a predetermined interval;
   selecting a first pulse wave and a second pulse wave from among a plurality of pulse waves measured by the plurality of pulse wave measuring sensors;
   analyzing the selected first pulse wave and second pulse wave; and
   determining a blood pressure based on an analysis result of the first pulse wave and the second pulse wave,
   wherein the grip-type blood pressure measuring apparatus has a cylinder shape, and the pulse wave measuring sensor array is a ring type array arranged to surround a cylindrical surface of the grip-type blood pressure measuring apparatus.

8. A grip-type blood pressure measuring apparatus, comprising:
   a pulse wave measuring sensor array comprising a plurality of pulse wave measuring sensors that are spaced apart from each other at a predetermined interval and are arranged on an external surface of a ring-type strip that is curved in a three-dimensional space to have a three-dimensional shape; and
   a blood pressure measurer configured to obtain a plurality of pulse waves from the plurality of pulse wave measuring sensors when the plurality of pulse wave measuring sensors on the ring-type strip are in contact with a user, select a first pulse wave and a second pulse wave from among the plurality of pulse waves, analyze the selected first pulse wave and second pulse wave, and determine a blood pressure based on an analysis result of the first pulse wave and the second pulse wave.

9. The apparatus of claim 8, wherein the plurality of pulse wave measuring sensors are arranged in a circumferential direction of the ring-type strip.

10. The apparatus of claim 8, wherein the blood pressure measurer comprises:
    a pulse wave selector configured to select the first pulse wave and the second pulse wave from among the plurality of pulse waves measured by the plurality of pulse wave measuring sensors;
    a feature point extractor configured to extract a first feature point from the first pulse wave and extract a second feature point corresponding to the first feature point from the second pulse wave; and
    a blood pressure calculator configured to calculate the blood pressure based on the first feature point and the second feature point.

11. The apparatus of claim 10, wherein the blood pressure calculator is further configured to calculate a pulse wave velocity based on the first feature point and the second feature point, and calculate blood pressure based on the calculated pulse wave velocity and a blood pressure estimation equation.

12. The apparatus of claim 11, wherein the blood pressure calculator is further configured to calculate a time difference between the first feature point and the second feature point, calculate a distance between a point where the first pulse wave is measured and a point where the second pulse wave is measured, and obtain the pulse wave velocity by dividing the distance by the time difference.

13. The apparatus of claim 10, wherein the pulse wave selector is further configured to detect a start point and an end point of pulse wave detection of the subject according to a movement of the plurality of pulse waves, and select a pulse wave measured at the start point of the pulse wave detection as the first pulse wave and a pulse wave measured at the end point of the pulse wave detection as the second pulse wave.

14. The apparatus of claim 8, further comprising a driver configured to generate a driving signal to drive the grip-type blood pressure measuring apparatus by sensing whether the user grips the grip-type blood pressure measuring apparatus.

15. The apparatus of claim 8, further comprises a user interface configured to output information on the blood pressure.

16. The apparatus of claim 8, further comprising a communicator configured to transmit the information on the blood pressure to an external device.

17. A grip-type blood pressure measuring apparatus, comprising:

a pulse wave measuring sensor array comprising a plurality of pulse wave measuring sensors that are spaced apart from each other at a predetermined interval; and a blood pressure measurer configured to select a first pulse wave and a second pulse wave from among a plurality of pulse waves measured by the plurality of pulse wave measuring sensors, analyze the selected first pulse wave and second pulse wave, and determine a blood pressure based on an analysis result of the first pulse wave and the second pulse wave, wherein the grip-type blood pressure measuring apparatus has a cylinder shape, and the pulse wave measuring sensor array is a ring type array arranged to surround a cylindrical surface of the grip-type blood pressure measuring apparatus.

* * * * *